(12) United States Patent
Ellingsen

(10) Patent No.: US 6,406,461 B1
(45) Date of Patent: Jun. 18, 2002

(54) ARRANGEMENT IN A NEEDLE HOLDER FOR A SELF-DESTRUCTING SYRINGE

(75) Inventor: Olav Ellingsen, Florø (NO)

(73) Assignee: Lifecare A.S., Floro (NO)

( * ) Notice: Subject to any disclaimer, the term of this patent is extended or adjusted under 35 U.S.C. 154(b) by 0 days.

(21) Appl. No.: 09/530,439

(22) PCT Filed: Nov. 4, 1998

(86) PCT No.: PCT/NO98/00333

§ 371 (c)(1),
(2), (4) Date: Apr. 28, 2000

(87) PCT Pub. No.: WO99/25401

PCT Pub. Date: May 27, 1999

(30) Foreign Application Priority Data

Nov. 5, 1997 (NO) .......................................... 19975103

(51) Int. Cl.⁷ ................................................. A61M 5/00
(52) U.S. Cl. ...................................... 604/263; 604/110
(58) Field of Search ............................... 604/110, 263, 604/195, 198, 218, 192; 128/919

(56) References Cited

U.S. PATENT DOCUMENTS 5,188,614 A * 2/1993 Hart ........................ 604/110 X

* cited by examiner

Primary Examiner—Anhtuan T. Nguyen
(74) Attorney, Agent, or Firm—Welsh & Katz, Ltd.

(57) ABSTRACT

An arrangement in a needle holder unit capable of being mounted on a syringe housing for self-destructing hypodermic and similar syringes wherein the needle holder is equipped with medically acceptable chemical agents for retracting the needle holder into the syringe housing.

2 Claims, 3 Drawing Sheets

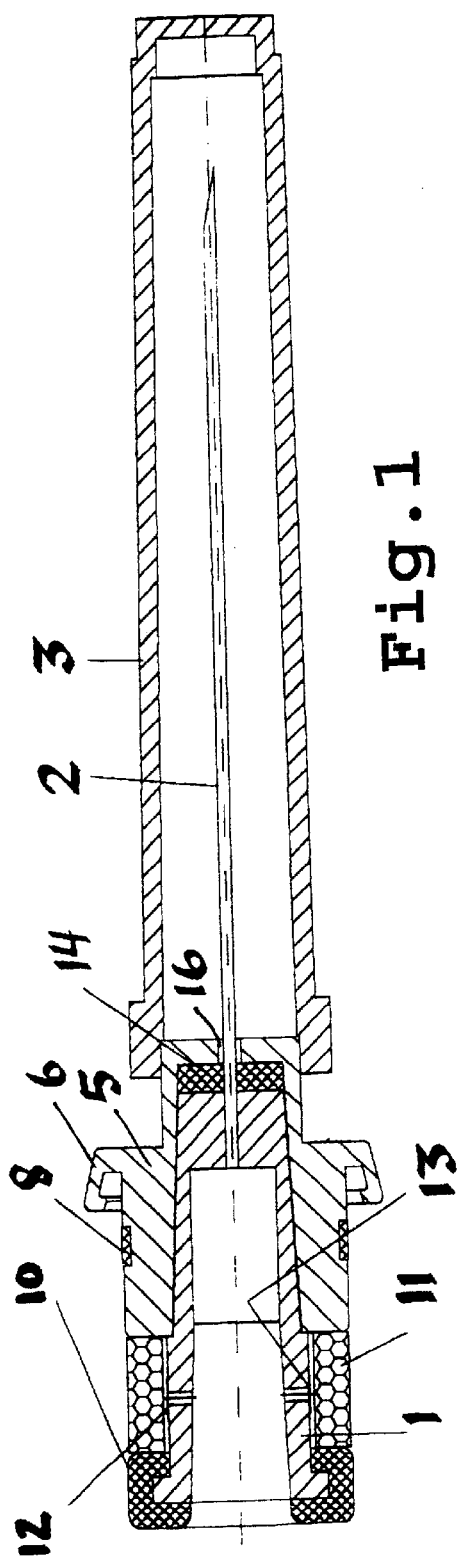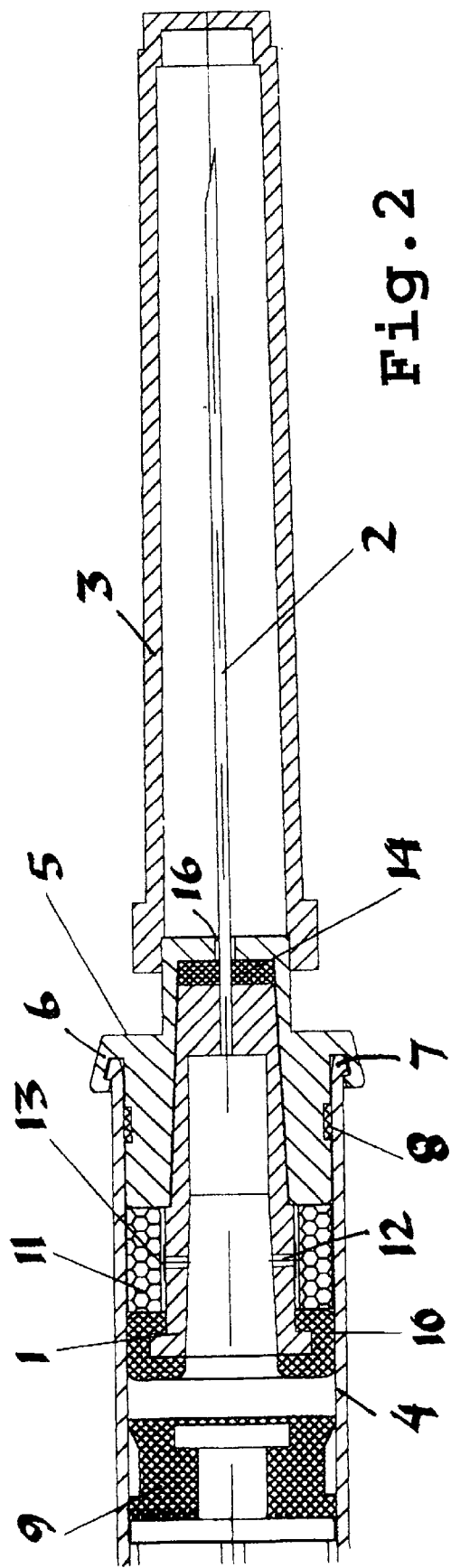

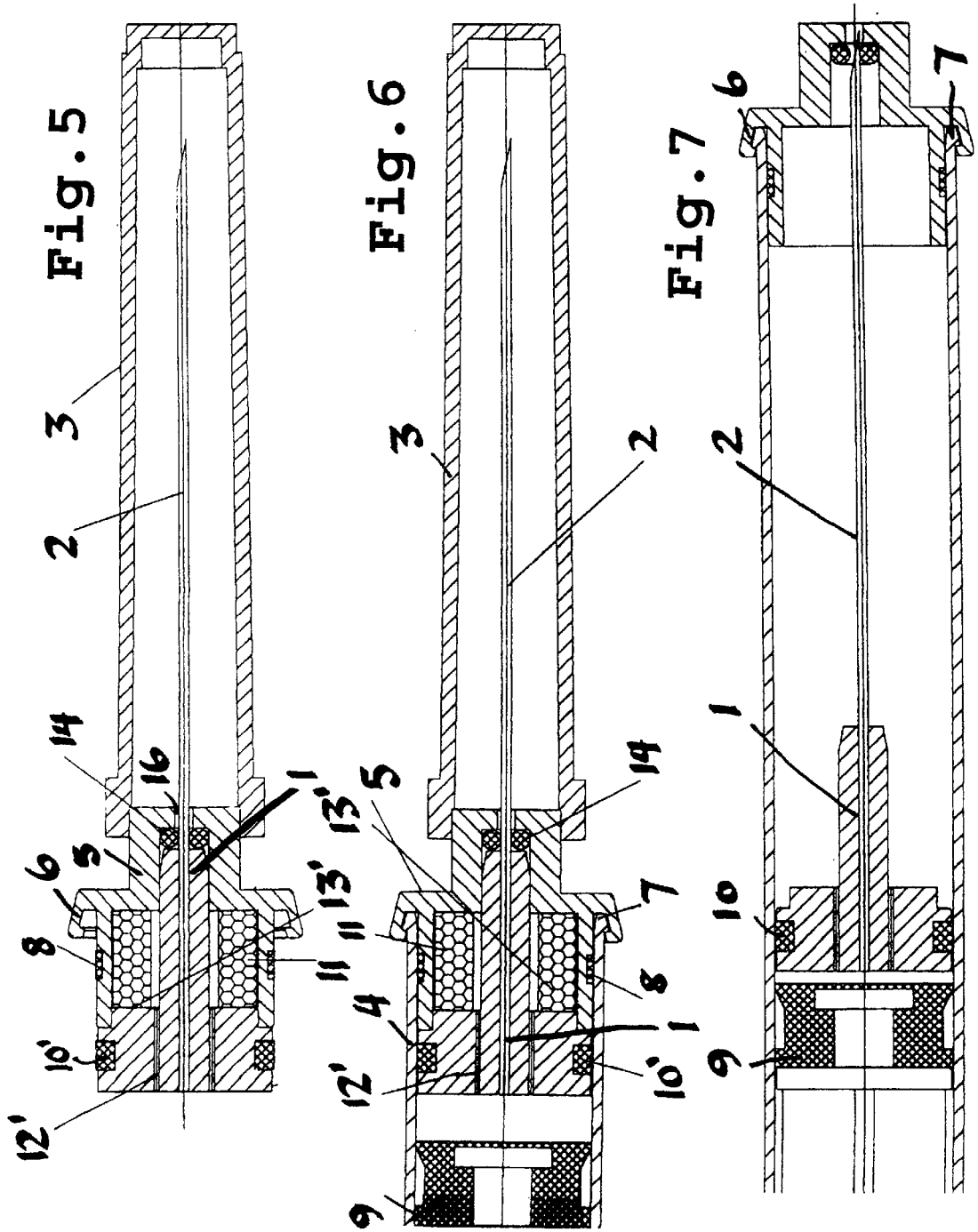

ARRANGEMENT IN A NEEDLE HOLDER FOR A SELF-DESTRUCTING SYRINGE

The present invention relates to an arrangement in a so-called one-use syringe or self-destructing syringe, especially a self-destructing hypodermic syringe of the type which generally comprises a syringe housing, a plunger with plunger rod, a plunger head with associated seal and an injection needle.

To be more specific, the invention relates to an arrangement in a needle holder for a syringe of this kind wherein the needle holder is equipped with means which render the syringe self-destructing.

The syringe is of the type that is destroyed on use and which then can be easily disposed of as the injection needle is withdrawn into the syringe housing on destruction of the syringe.

Disposable or self-destructing syringes are enjoying an ever-growing market, not least because it has become very much more common for sick persons to inject themselves. This is true in the case of, e.g., diabetic patients.

However, there is also a large an undesirable market for hypodermic syringes, namely addicts who take drugs by injection, and this user category in particular has been highly exposed to various illnesses the transmission of which is due to uncritical use of syringes.

The need for inexpensive and simple, but nevertheless dependable, self-destructing disposable syringes is therefore still very great, as an element in the battle against the spread of disease by transmission via the blood stream due to the aforementioned uncritical use of syringes.

As examples of the most common, infectious diseases today which are thus transmitted today, mention can be made of hepatitis B and AIDS.

There are various auto-destruct hypodermic syringes on the market and several syringes are known, for example, that are of the type which have a frangible member that is broken after the syringe has been used for the first time.

Many of the proposed solutions have either been too costly or too unsafe as it has been possible to manipulate the syringe so as to render it re-usable.

As regards syringes of this kind, reference will be made to NO 163 263-B and NO 301 523-C.

Another type of syringe is described in Norwegian Application 970576. This application describes syringes of the type wherein the needle holder and needle are secured to the syringe against a force which is released when the injection has been given, and wherein the needle holder and needle are withdrawn into the syringe which may then be easily disposed of.

The present invention is a further development of the technology described in P970576.

The syringes described in P970576 are simple, safe to use and safe to dispose of. However, they necessitate the availability of a large number of complete syringes.

However, the market has expressed a need to be able to equip a standard syringe housing with a mountable injection needle which is chosen according to need, yet without having to forgo the self-destructing properties of the earlier syringes.

The object of the present invention is to provide a syringe of this kind.

Accordingly, the present invention relates to an arrangement in a needle holder unit capable of being mounted on a syringe housing for self-destructing hypodermic and similar syringes, and the invention is characterised in that the needle holder is equipped with medically acceptable chemical agents for retracting the needle holder into the syringe housing.

The preferred propellant-generating chemical is crystalline formic acid and calcium carbonate and/or another similar compound which on the penetration of moisture gives off $CO_2$ as a propellant gas.

The invention will be illustrated in more detail by means of the attached figures, wherein:

FIG. 1 shows a first embodiment of a needle holder unit in the form in which it can be supplied;

FIG. 2 shows the needle holder unit of FIG. 1, pushed inside a syringe housing and wherein the plunger has been moved forward;

FIG. 5 shows a third embodiment of a needle holder according to the invention;

Figure 3:
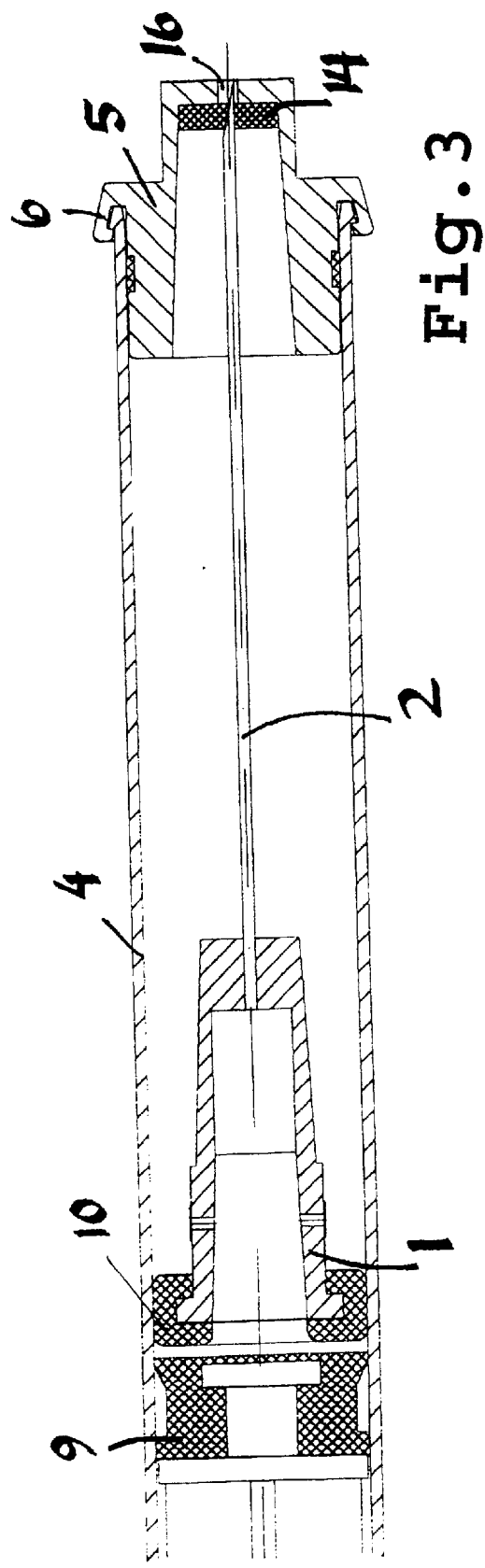
FIG. 3 shows a used needle holder according to FIGS. 1 and 2 once destroyed, pushed inside the housing.

FIG. 6 corresponds to FIG. 2 and shows the needle holder of FIG. 5 mounted in a syringe housing and wherein the plunger has been moved forward; and FIG. 7 corresponds to FIG. 3 with the needle holder of FIGS. 5 and 6 once destroyed, pushed inside the plunger housing.

As indicated above, the present invention is a further development of the technology described in NO-P 970576, in particular the alternative shown in FIG. 5 in this application and described in claims 3–5 therein.

The present invention is based on the need to be able to take a standard plunger housing and the equipment associated therewith as a point of departure and at the same time to be able to have at one's disposal a wide range of different needles, yet without having to forgo the self-destructing properties which today must virtually be considered as a requirement, or at least as a major advantage.

In the figures, the same items have been given the same reference numerals as far as possible.

FIG. 1 shows a needle holder unit having a needle holder 1 and a needle 2.

The needle is protected in the usual fashion by a protective cover 3.

To retain the needle holder 1 and needle 2 in a syringe housing 4, the needle holder is located in a cap 5 equipped with a claw-like clamp 6, designed to grip around a bead 7 (FIGS. 2 and 6) along the exterior of the mouth of the plunger housing 4.

Tightness between the cap 5 and the interior of the plunger housing 4 is achieved with the aid of suitable seals 8.

In the end facing the plunger 9, the needle holder is equipped with a gasket 10.

In a seat formed between the rear end of the cap 5 and the gasket 10, a seat which has the form of a circumferential groove, there is provided an agent 11 which on contact with the liquid injection fluid gives off a propellant gas.

The outer periphery of the "block" of chemical compound 11 may be slightly smaller than the outer diameter defined by the gaskets 8 and 10 as in principle it is between these seals that pressure is exerted from the gas generated from the compound 11.

This means that, if desirable, it is possible to provide a shield around the compound 11 to prevent the inadvertent admission of moisture.

FIG. 2 shows the situation when the injection is almost complete. The plunger 9 has been pressed almost to the bottom of the housing 4 and some injection liquid is pressed into the groove 12 provided in the needle holder 5 and which connects the interior of the syringe with the compound 11 for the generation of propellant gas.

On the side facing towards the compound 11 there is provided a reflux valve, for example, in the form of a flexible, elastic flap.

When, due to the low overpressure in the syringe, some injection liquid is pressed inside through the channel 12, the flap 13 will be lifted slightly and allow injection liquid to act on the compound 11 which then in turn generates propellant gas This gas will then force the needle holder 1 and the needle 2 away from the cap 5 and into the plunger housing 4.

Of course, the needle must be able to slide freely through the opening 16 in the cap 5, and for this reason a gasket 14 that is known per se is arranged inside the cap 5 to ensure the desired tightness.

Figure 4:
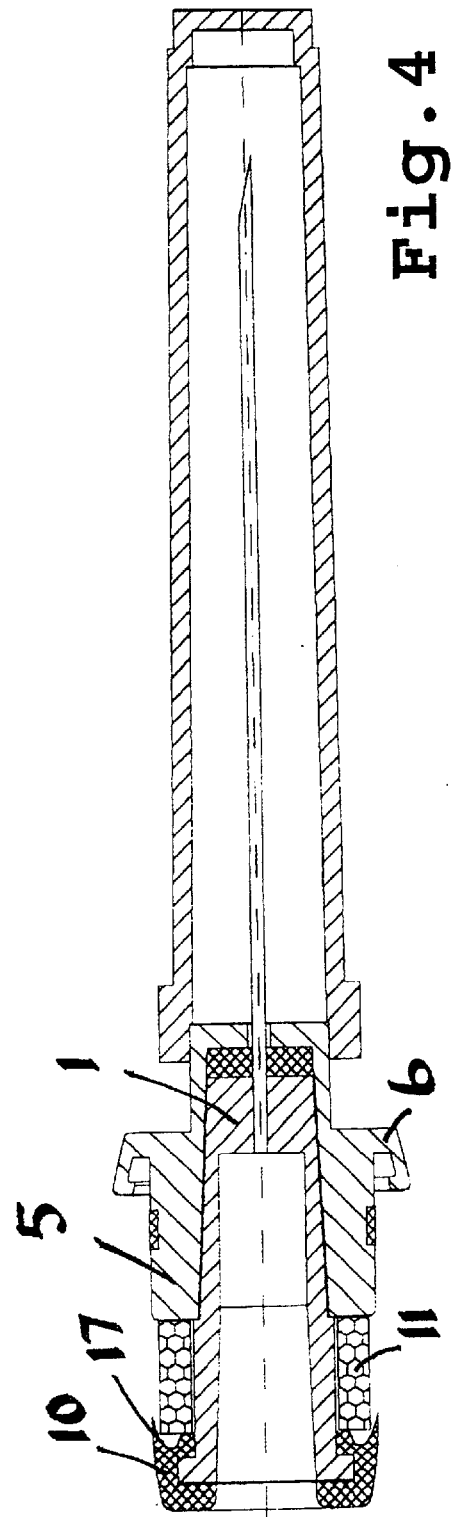
FIG. 4 shows a second embodiment of a needle holder according to the invention.

FIG. 4 shows an alternative embodiment of the needle holder in FIG. 1.

In this case, however, the channel 12 and reflux valve 13 have been omitted and the gasket 10 converted into a combined gasket and reflux valve, which is achieved by making the front end of the gasket in the form of a flap 17 which extends forward and rests tightly against the inside of the syringe housing.

FIG. 5 shows another embodiment of the invention. In this embodiment, however, the chemical compound 11 is placed in a circular channel located within the wall of the cap 5 but outside the needle holder 1. The needle holder 1 in this case is equipped with a rear block 1' through which, parallel to the needle 2, channels 12' run from the inside of the syringe housing to the space containing the chemical compound 11.

In this case, tightness is secured on the one side by the seal 8 on the cap 5 and a seal 9' on the block 1' of the needle holder 1.

Free access to the chamber containing the chemical compound 11 is also blocked in this case with the aid of a flap or membrane 13' acting as a reflux valve which, when an overpressure arise as the plunger 9 is moved towards the bottom, that is, towards the needle holder 1, is lifted and admits liquid into the compound, and wherein a reaction then takes place which generates a gas which in turn presses the needle holder, which in practice means the gasket 10', away from the cap and gasket 8 so that the needle holder 1 and the needle 2 are withdrawn into the plunger housing 4 for safe disposal.

The advantage of the embodiment according to FIG. 5 over that shown in FIGS. 1 and 4 respectively is that less injection liquid remains in the syringe.

Of course, a more compact embodiment of the needle holder in FIGS. 1 and 4, especially that in FIG. 4, is conceivable. However, this is a matter of balancing the advantages and disadvantages, where different factors must be taken into consideration, for example, desired weight, desired material consumption and the type and nature of the liquid which is to be injected or the need to adhere strictly to certain amounts.

Weighed against the advantages obtained by being able to work with a standard syringe housing, but being able to choose so freely between a wide range of injection needles, the invention provides a favourable, simple and inexpensive alternative in the case of self-destroying syringes, which is something that unfortunately has proven to be an absolute necessity in today's society.

What is claimed is:

1. A needle holder unit for self-destructing syringes, characterised in that it consists of a cap (5) for mounting on a syringe housing (4) and having a circular clamp (6) for attachment to the housing (4) and having a cylindrical portion with seals (8) against the inner surface of the housing (4);

a needle holder (1) and needle (2), having a cylindrical portion with seal (10') against the inner surface of the housing (4); and a medically acceptable chemical agent (11) positioned between the cap (5) and the needle holder (1) for retracting the needle holder (1) into the syringe housing (4), wherein the needle holder in addition is equipped with channels (12), (12') having one-way or reflux valves (13, (13') or similarly functioning seals (10, 17) which in use conduct the liquid to the agent (11).

2. An arrangement according to claim 1, characterised in that the chemical agent is based on carbonate and crystalline tartaric acid.

\* \* \* \* \*